| United States Patent [19] | [11] 3,947,515 |
|---|---|
| Miedtank et al. | [45] Mar. 30, 1976 |

[54] PROCESS FOR THE PREPARATION OF PURE, AROMATIC o-HYDROXY-CARBOXYLIC ACID ARYL AMIDES

[75] Inventors: Sighart Miedtank, Dreieichenhain; Adam Rüffer, Hofheim, Taunus; Hans Galster, Frankfurt am Main, all of Germany

[73] Assignee: Hoechst Aktiengesellschaft, Frankfurt am Main, Germany

[22] Filed: Feb. 4, 1975

[21] Appl. No.: 546,932

[30] Foreign Application Priority Data

Feb. 8, 1974 Germany............................ 2405986

[52] U.S. Cl............................... 260/559 S; 260/560
[51] Int. Cl.$^2$........................................ C07C 102/04
[58] Field of Search.............. 260/559 S, 560, 559 R

[56] References Cited
UNITED STATES PATENTS

| 1,909,960 | 5/1933 | Hitch | 260/560 |
|---|---|---|---|
| 1,935,930 | 11/1933 | Zitscher et al. | 260/560 |
| 2,022,579 | 11/1935 | Turski | 260/560 |
| 2,097,915 | 11/1937 | Dahlen et al. | 260/560 |
| 2,410,397 | 10/1946 | Weiss et al. | 260/559 S |
| 2,636,900 | 4/1953 | Rambacher et al. | 260/559 S |
| 2,691,041 | 10/1954 | Clinton et al. | 260/559 S |
| 2,763,683 | 9/1956 | Beman et al. | 260/559 S |

*Primary Examiner*—Allen B. Curtis
*Attorney, Agent, or Firm*—Connolly and Hutz

[57] ABSTRACT

Process for the preparation of pure aromatic o-hydroxy-carboxylic acid aryl amides by condensing an aromatic o-hydroxy-carboxylic acid with an aryl amine in the presence of phosphorus chlorides in an organic solvent or diluent, which process comprises treating the reaction mixture or the reaction product with 1 to 25 %, calculated on the weight of the reaction product, of an aliphatic amino-polycarboxylic acid as chelate forming agent. It is not necessary to purify the products, because they are obtained in such a pure form that they can be used directly as coupling components for azo pigments.

10 Claims, No Drawings

PROCESS FOR THE PREPARATION OF PURE, AROMATIC O-HYDROXY-CARBOXYLIC ACID ARYL AMIDES

The present invention relates to an improved process for the preparation of aromatic o-hydroxy-carboxylic acid aryl amides which allows to obtain them in pure form.

Aryl amides of aromatic o-hydroxy-carboxylic acids are largely used for the preparation of water-insoluble azo dyestuffs on the fiber (cf. L. Diserens, Die neuesten Fortschritte in der Anwendung der Farbstoffe, 3rd, edition, part 1, volume 1 (1951), pages 507 et seq.; Colour Index, 3rd edition (1971), C.I. No. 37 505 to 37 608), further for the preparation of azo pigments (cf. H.A. Lubs, The Chemistry of Synthetic Dyes and Pigments (1955), pages 634 to 635; Colour Index, 3rd edition (1973), C.I. No. 12,300 to 12,505; Ullmanns Enzyclopaedie der technischen Chemie, volume 4 (1953), pages 155 and 156), further as coupling agent for colors in color photography (cf. U.S. Pat. No, 2,706,684) and as ultraviolet absorbers (cf. German Patent No, 1,144,726).

In industry, they are generally prepared by reacting aromatic o-hydroxy-carboxylic acids with aryl amines in the presence of phosphorus chlorides, especially, phosphorus trichloride, in an organic solvent or diluent, for example, toluene or xylene (cf. Ullmanns Enzyklopaedie der technischen Chemie, Vol. 12 (1960), pages 607–609; K. Venkataraman, The Chemistry of Synthetic Dyes, Vol. I (1952), page 655). According to this process, the o-hydroxy-carboxylic acid aryl amides are obtained in a quality generally sufficient for the preparation of water-insoluble azo dyestuffs on the fiber, because the by-products formed do not cause any trouble in the usual dyeing and printing processes. However, they can be very troublesome when the o-hydroxy-carboxylic acid aryl amides are used for the preparation of azo pigments, because not only the shade, but also the grain hardness, the finishing behavior and the fastness properties, for example the fastness to solvents, of the azo pigments are adversely affected by these impurities.

For this reason, the o-hydroxy-carboxylic acid aryl amides used for the preparation of azo pigments must be purified in many cases to obtain the degree of purity required. They can be purified by dissolving them in aqueous alkali metal hydroxide solutions, for example, sodium hydroxide solution or potassium hydroxide solution, followed by fractional precipitation with acids, or by treating them with aqueous solutions of weak alkalis, for example an aqueous solution of sodium carbonate, or by extraction with organic solvents (cf. U.S. Pat. No. 1,890,202). When purifying in this manner, losses in o-hydroxy-carboxylic acid aryl amides are inevitable and additional operations are required that are expensive and uncomfortable.

Now, it was found that aromatic o-hydroxy-carboxylic acid aryl amides can be prepared in the pure form required for azo pigments and the drawbacks in their synthesis mentioned can be avoided by condensing aromatic o-hydroxy-carboxylic acids with aryl amines in the presence of phosphorus chlorides in an organic solvent or diluent, when the condensation products are treated with a chelate forming agent.

In general, the process of the invention is carried out by reacting the aromatic o-hydroxy-carboxylic acid, as usual, with the aryl amine in the presence of a phosphorus chloride, especially phosphorus trichloride, in an organic solvent or diluent, for example, toluene, xylene, mono or dichlorobenzene, adding to this reaction mixture a chelate forming agent, advantageously in the form of an alkaline solution, and distilling off the organic solvent or diluent with steam. The precipitated o-hydroxy-carboxylic acid aryl amide is filtered off, washed with water and dried.

The products obtained according to the known method without the addition of a chelate forming agent can also be purified by treating the reaction product after filtration or drying with an alkaline aqueous solution of the chelate forming agent, preferably at a temperature ranging from 60° to 100°C, filtering off the separated aryl amide, washing it with water and drying it. Moreover, the chelate forming agent can be added to the reaction mixture or already to one of the reaction components before condensation.

The products of the invention are generally treated in the alkaline range, i.e. from a pH above 7 to 14.

The improved process of the invention for the preparation of pure aromatic o-hydroxy-carboxylic acid aryl amides is independent of the nature of the aromatic o-hydroxy-carboxylic acids or aryl amines used for the preparation of the pure end product desired, however, of the aromatic o-hydroxy-carboxylic acids are especially suitable the 2-hydroxynaphthalene-3-carboxylic acid and its substitution products, such as the 6-alkyl, 6-alkoxy, 6-halogen and 6-nitro-2-hydroxy-naphthoic acids, alkyl, alkoxy preferably being alkyl and alkoxy groups of 1 to 4 carbon atoms and halogen atoms preferably chlorine and bromine atoms; furthermore, salicylic acid, para-cresotic acid, 2-hydroxyanthracene-3-carboxylic acid, 3-hydroxy-fluorene-2-carboxylic acid, 4-hydroxy-diphenyl-3-carboxylic acid and aromatic-heterocyclic o-hydroxy-carboxylic acids, for example, from the dibenzofurane, carbazole or benzocarbazole series can be used.

Of the great number of aryl amines suitable for the preparation of the aryl amides in question, there are especially to be mentioned aniline, the dichloroanilines, toluidines, xylidines, anisidines, phenetidines, nitranilines, chlorotoluidines, chloroanisidines, dimethoxy anilines, chlorodimethoxy anilines, methoxy methyl anilines, aminonaphthalenes, aminomethoxy diphenylene oxides, aminobenzthiazoles or aminopyrenes. Above all, the process of the invention generally applies for the preparation of pure o-hydroxy-carboxylic acid aryl amides which correspond to the following general formula:

in which the hydroxy group in A is in o-position to the carbonamide group and A stands for a benzene nucleus or a naphthalene nucleus, which can be substituted by alkyl, alkoxy or nitro groups and/or halogen atoms, especially, in addition to the nitro group, alkyl groups of 1 to 4 carbon atoms, the methyl and ethyl groups being preferred, alkoxy groups of 1 to 4 carbon atoms, the methoxy and ethoxy group being preferred, as well as chlorine or bromine atoms; and B stands for the phenyl or naphthyl radical which can be substituted by chlorine or bromine atoms, alkyl groups of 1 to 4 carbon atoms, especially methyl and ethyl groups, alkoxy groups of 1 to 4 carbon atoms, especially methoxy and ethoxy groups and/or nitro groups.

Chelate forming agents suitable for the process of the invention are especially polycarboxylic acids or aminopolycarboxylic acids and the salts thereof, especially the alkali metal or alkaline earth metal salts. In general, especially suitable chelate forming agents are aliphatic hydroxy-carboxylic acids of 3 to 7 carbon atoms which contain 2 to 4 carboxy groups and 2 to 5 hydroxy groups, each carbon atom carrying only one hydroxy or carboxylic acid group, and aliphatic amine compounds which contain alkyl radicals of 1 to 4 carbon atoms and 1 to 4 nitrogen atoms, in which case the alkyl radicals can be linked with each other via nitrogen atoms and at least two of these alkyl radicals are substituted by carboxy and/or hydroxy groups. Of these compounds, there are especially to be mentioned citric acid, ethylene-diaminetetraacetic acid, diethylene-triamine pentaacetic acid, 1,3-diamino-2-hydroxypropane-N,N,N,N-tetraacetic acid, nitrilotriacetic acid, N,N-di-(β-hydroxyethyl)-glycine and N-(β-hydroxyethyl)-ethylene diamine-triacetic acid. Preferred chelate forming agents are ethylene diamine-tetraacetic acid and nitrilotriacetic acid in the form of their sodium salts.

In the process of the invention, the chelate forming agent is generally used in amounts of about 1 to 25 %, preferably about 3 to 13 %, calculated on the weight of the aromatic O-hydroxy-carboxylic acid-aryl amide to be prepared or which is already prepared.

The chelate forming agent can be used in liquid form or as flocks or powder.

The following Examples illustrate the invention, the parts and percentages are by weight, unless otherwise stated, the ratio of parts by weight to parts by volume being that of the kilogram to the liter.

EXAMPLE 1

In a vessel 1000 parts of 2-hydroxynaphthalene-3-carboxylic acid diluted in 6000 parts by volume of toluene were condensed with 520 parts of aniline in the presence of 320 parts of phosphorus trichloride. Then, the reaction mixture was introduced with pressure into a mixture of 300 parts of sodium carbonate and 50 parts of the sodium salt of ethylene diamine tetraacetic acid in 1500 parts of water, the toluene was distilled off with steam, the precipitated 2-hydroxynaphthalene-3-carboxylic acid anilide was filtered off in a filter press, washed with hot water and dried. 1300 parts of pure 2-hydroxynaphthalene-3-carboxylic acid anilide were obtained which could directly be used for the preparation of azo pigments.

EXAMPLE 2

1000 Parts of 2-hydroxynaphthalene-3-carboxylic acid diluted in 6000 parts by volume of toluene were condensed in a vessel with 520 parts of aniline in the presence of 320 parts of phosphorus trichloride. Then, the reaction mixture was introduced with pressure into a mixture of 300 parts of sodium carbonate and 50 parts of nitrilotriacetic acid in 1500 parts of water, the toluene was distilled off with steam, the precipitated 2-hydroxynaphthalene-3-carboxylic acid anilide was filtered off in a filter press, washed with hot water and dried. 1300 parts of pure 2-hydroxynaphthalene-3-carboxylic acid anilide were obtained which could directly be used for the preparation of azo pigments.

EXAMPLE 3

980 Parts of 2-hydroxynaphthalene-3-carboxylic acid diluted in 5000 parts by volume of toluene and 453 parts of 45 % sodium hydroxide solution were reacted in a vessel to yield the sodium salt of 2-hydroxynaphthalene-3-carboxylic acid. This reaction mixture was dehydrated by means of azeotropic distillation. Then, 600 parts of o-toluidine were added and the mixture was reacted in the presence of 297 parts of phosphorus trichloride. Then, the reaction mixture was introduced with pressure into a mixture of 240 parts of sodium carbonate, 8 parts of sodium dithionite and 60 parts of the sodium salt of ethylene diaminetetraacetic acid in 1200 parts of water, the toluene was distilled off with steam, the precipitated 2-hydroxynaphthalene-3-carboxylic acid-(2'-methyl)-anilide was filtered off in a filter press, washed with hot water and dried. 1330 parts of pure 2-hydroxynaphthalene-3-carboxylic acid (2'-methyl)-anilide were obtained which could directly be used for the preparation of azo pigments.

EXAMPLE 4

980 Parts of 2-hydroxynaphthalene-3-carboxylic acid diluted in 5000 parts by volume of toluene and 453 parts of 45 % sodium hydroxide solution were reacted in a vessel to yield the sodium salt of 2-hydroxynaphthalene-3-carboxylic acid. This reaction mixture was dehydrated by means of azeotropic distillation. Then, 600 parts of o-toluidine were added and the mixture was condensed in the presence of 297 parts of phosphorus trichloride. Then, the reaction mixture was introduced with pressure into a mixture of 240 parts of sodium carbonate, 8 parts of sodium dithionite and 60 parts of nitrilotriacetic acid in 1200 parts of water, the toluene was distilled off with steam, the precipitated 2-hydroxynaphthalene-3-carboxylic acid (2'-methyl)-anilide was filtered off in a filter press, washed with hot water and dried. 1330 parts of pure 2-hydroxynaphthalene-3-carboxylic acid-(2'-methyl)-anilide were obtained which could directly be used for the preparation of azo pigments.

EXAMPLE 5

1000 Parts of 2-hydroxynaphthalene-3-carboxylic acid diluted in 6000 parts by volume of toluene were condensed in a vessel with 520 parts of aniline in the presence of 320 parts of phosphorus trichloride. Then, the reaction mixture was introduced with pressure into a solution of 300 parts of sodium carbonate in 1500 parts of water, the toluene was distilled off with steam, the precipitated 2-hydroxynaphthalene-3-carboxylic acid anilide was filtered off in a filter press and washed with hot water. Then, the moist product was introduced into a solution of 300 parts of sodium carbonate and 50 parts of the sodium salt of ethylene diaminetetraacetic acid in 1500 parts of water, the mixture was heated to 90°–100°C and stirred for half an hour to 3 hours. Thereafter, the 2-hydroxynaphthalene-3-carboxylic acid anilide was again filtered off in a filter press, washed with hot water and dried. 1300 parts of pure 2-hydroxynaphthalene-3-carboxylic acid anilide were obtained which could directly be used for the preparation of azo pigments.

EXAMPLE 6

980 Parts of 2-hydroxynaphthalene-3-carboxylic acid diluted in 5000 parts by volume of toluene and 453 parts of 45 % sodium hydroxide solution were reacted in a vessel to yield the sodium salt of 2-hydroxynaphthalene-3-carboxylic acid. This reaction mixture was dehydrated by means of azeotropic distillation. Then, 600 parts of o-toluidine were added and the mixture was condensed in the presence of 297 parts of phosphorus trichloride. Then, the reaction mixture was introduced with pressure into a solution of 240 parts of sodium carbonate and 8 parts of sodium dithionite in 1200 parts of water, the toluene was distilled off with steam, the precipitated product was filtered off in a filter press and washed with hot water. After this isolation, the moist 2hydroxy-naphthalene-3-carboxylic acid-(2'-methyl)-anilide was introduced into a solution of 300 parts of sodium carbonate and 60 parts of nitrilotriacetic acid in 1200 parts of water, heated to about 90°–100°C and stirred for half an hour to 3 hours. Then, the product was again filtered off in a filter press, washed with hot water and dried. 1330 parts of pure 2-hydroxynaphthalene-3-carboxylic acid-(2'-methyl)-anilide were obtained which could directly be used for the preparation of azo pigments.

In an analogous manner, other 2-hydroxynaphthalene-3-carboxylic acid aryl amides used for the preparation of azo pigments can be obtained in pure form, for example, 2-hydroxynaphthalene-3-carboxylic acid-(2',5'-dimethoxy)-anilide, 2-hydroxynaphthalene-3-carboxylic acid-(2'-ethoxy)-anilide, 2-hydroxynaphthalene-3-carboxylic acid-(4'-chloro)-anilide, 2-hydroxynaphthalene-3-carboxylic acid-(2',5'-dimethoxy-4'-chloro)-anilide, 2-hydroxynaphthalene-3-carboxylic acid-(2',4'-dimethoxy-5'-chloro)-anilide, 2-hydroxynaphthalene-3-carboxylic acid-(2'-methyl-5'-chloro)-anilide, 2-hydroxynaphthalene-3-carboxylic acid-(2'-methoxy)-anilide, 2-hydroxynaphthalene-3-carboxylic acid-(4'-methyl)-anilide, 2-hydroxynaphthalene-3-carboxylic acid-(2'-methyl-4'-chloro)-anilide or 2-hydroxynaphthalene-3-carboxylic acid-(4'-acetamino)-anilide.

EXAMPLE 7

785 Parts of 2-hydroxynaphthalene-3-carboxylic acid and 361 parts of 45 % sodium hydroxide solution were reacted in a vessel in the presence of 20 parts of the sodium salt of ethylene diaminetetraacetic acid in 5000 parts by volume of toluene to yield the sodium salt of 2-hydroxynaphthalene-3-carboxylic acid; then the reaction mixture was dehydrated by means of azeotropic distillation. Then, 570 parts of o-phenetidine were added and the mixture was condensed in the presence of 297 parts of phosphorus trichloride. Thereafter, the reaction mixture was introduced with pressure into a mixture of 240 parts of sodium carbonate, 8 parts of sodium dithionite and 80 parts of the sodium salt of ethylene diaminetetraacetic acid in 1200 parts of water, the toluene was distilled off with steam, the precipitated 2-hydroxynaphthalene-3-carboxylic acid-(2'-ethoxy)-phenyl amide was filtered off in a filter press, washed with hot water and dried.

1200 Parts of 2-hydroxynaphthalene-3-carboxylic acid-(2'-ethoxy)-phenyl amide were obtained which could directly be used for the preparation of azo pigments.

We claim:
1. In a process for the preparation of an aromatic o-hydroxy-carboxylic acid aryl amide by condensing an aromatic o-hydroxy-carboxylic acid with an aryl amine in the presence of phosphorus chlorides in an organic solvent or diluent, the improvement comprising adding to the reaction mixture or the reaction product 1 to 25 %, calculated on the weight of the reaction product, of an aliphatic aminopolycarboxylic acid or an alkali metal or alkaline earth metal salt thereof as chelate forming agent.

2. The process as claimed in claim 1, wherein the compound prepared has the formula

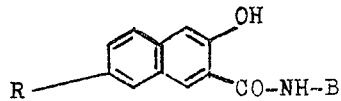

in which R is hydrogen, lower alkyl, lower alkoxy, nitro, chlorine or bromine and B is an aryl radical, and is prepared from a compound of the formula

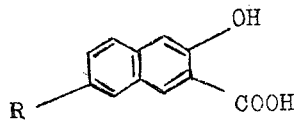

in which R is defined as above, and an arylamino compound.

3. The process as claimed in claim 2, wherein B is phenylene or naphthylene or phenylene or naphthalene substituted by one, two or three substituents selected from chlorine, bromine, lower alkyl, lower alkoxy and nitro.

4. The process as claimed in claim 1, wherein the aliphatic aminopolycarboxylic acid has the formula

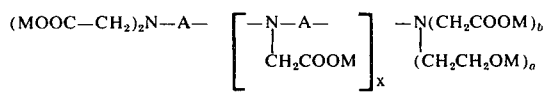

in which M is hydrogen, sodium or potassium, A is alkylene or hydroxyalkylene of 2 to 4 carbon atoms, $x$ is zero, 1 or 2, $a$ is zero, 1 to 2 and $b$ is $2-a$.

5. The process as claimed in claim 1, wherein the aliphatic aminopolycarboxylic acid has the formula

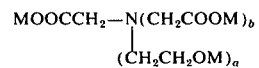

in which M is hydrogen, sodium or potassium, $a$ is zero, 1 or 2 and $b$ is $2-a$.

6. The process as claimed in claim 4, wherein the aliphatic polycarboxylic acid is ethylenediamine tetraacetic acid, diethylenetriamine pentaacetic acid, 1,3-diamino-2-hydroxypropane-N,N,N,N-tetraacetic acid, N-(β-hydroxyethyl)-ethylene diamine triacetic acid or a sodium or potassium salt of said acids.

7. The process as claimed in claim 5, wherein the aliphatic amino-polycarboxylic acid is nitrilotriacetic acid, N,N-di-(β-hydroxyethyl)-glycine or a sodium or potassium salt of said acids.

8. The process as claimed in claim 1, wherein the aliphatic aminopolycarboxylic acid is ethylenediamine tetraacetic acid, nitrilo triacetic acid or a sodium salt thereof.

9. The process as claimed in claim 1, wherein 3 to 13 %, calculated on the weight of the product, of aliphatic aminopolycarboxylic acid are added.

10. The process as claimed in claim 1, wherein the pH value is in the range of 7 to 14.

* * * * *